US012254972B2

(12) United States Patent
Young et al.

(10) Patent No.: US 12,254,972 B2
(45) Date of Patent: Mar. 18, 2025

(54) GENERATING RECOMMENDATIONS BASED ON NUTRITIONAL PRESCRIPTIONS

(71) Applicant: SeekingSimple, Inc., Eagle, ID (US)

(72) Inventors: Clay H Young, McCall, ID (US); Mark Eisner, Framingham, MA (US)

(73) Assignee: SeekingSimple, Inc., Eagle, ID (US)

( * ) Notice: Subject to any disclaimer, the term of this patent is extended or adjusted under 35 U.S.C. 154(b) by 301 days.

(21) Appl. No.: 17/681,286

(22) Filed: Feb. 25, 2022

(65) Prior Publication Data

US 2022/0270742 A1 Aug. 25, 2022

Related U.S. Application Data

(60) Provisional application No. 63/153,505, filed on Feb. 25, 2021.

(51) Int. Cl.
| | |
|---|---|
| *G16H 20/60* | (2018.01) |
| *A23L 33/00* | (2016.01) |
| *G01N 33/02* | (2006.01) |

(52) U.S. Cl.
CPC ............. *G16H 20/60* (2018.01); *A23L 33/30* (2016.08); *A23L 33/40* (2016.08); *G01N 33/02* (2013.01); *A23V 2002/00* (2013.01)

(58) Field of Classification Search
CPC ..................................................... G16H 20/60
See application file for complete search history.

(56) References Cited

U.S. PATENT DOCUMENTS

| | | | | |
|---|---|---|---|---|
| 11,862,037 | B1* | 1/2024 | Seymore | A61B 5/681 |
| 2008/0005082 | A1* | 1/2008 | Hughes | G16H 20/60 |
| 2013/0226729 | A1* | 8/2013 | Reed | G09B 19/0092 |
| | | | | 705/26.7 |
| 2018/0240359 | A1* | 8/2018 | Hujsak | G06N 5/022 |
| 2021/0134434 | A1* | 5/2021 | Riley | G16H 50/30 |
| 2021/0225052 | A1* | 7/2021 | Marzorati | G06N 20/00 |
| 2021/0375429 | A1* | 12/2021 | Franklin | G16H 70/20 |

OTHER PUBLICATIONS

Federica Cena, et al., Generating Recommendations from Multiple data sources: a methodological Framework for System Design and Its Application, Oct. 19, 2020 (Year: 2020).*

(Continued)

*Primary Examiner* — Evangeline Barr
(74) *Attorney, Agent, or Firm* — Andersen Gorecki, LLP

(57) ABSTRACT

A cloud-based application generates food product recommendations in support of medical nutritional therapy. The recommendations are calculated based on at least one patient-specific nutritional prescription and extended ingredient data that identifies food product ingredients or nutritional calculations that do not appear on packaging labels. The patient-specific nutritional prescription is calculated based on a patient profile and at least one nutritional prescription template. The recommendations may be used to perform a pantry makeover in which harmful food products are removed from household food storage and beneficial food products are added to household food storage. Recommendations may be calculated in real-time for food products that are identified during food shopping. Less harmful alternative food products are identified and suggested.

14 Claims, 15 Drawing Sheets

(56) References Cited

OTHER PUBLICATIONS

Federica Cena, et al., Generating Recommendations from Multiple data sources: a methodological Framework for System Design and lis Application, Oct. 19, 2020 (Year: 2020).*

Ellen Badinelli, ScanAvert: Detection and Alarm against Ingredient Harm, 2006, IEEE CCNC 2006 proceedings, pp. 1286-1287 (Year: 2006).*

* cited by examiner

GENERATING RECOMMENDATIONS BASED ON NUTRITIONAL PRESCRIPTIONS

TECHNICAL FIELD

The subject matter of this disclosure is generally related to computer systems and software for supporting nutritional therapy.

BACKGROUND

More than half of all adults living in the United States have a chronic condition such as metabolic syndrome, arthritis, cancer, chronic obstructive pulmonary disease, coronary heart disease, current asthma, diabetes, hepatitis, hypertension, stroke, and weak or failing kidneys. Medical nutritional therapy, which is nutrition-based treatment that enhances the consumption of disease-healthy ingredients and reduces or eliminates consumption of disease-unhealthy ingredients, can be an important part of the treatment for chronic disease conditions. For example, it is important that a patient suffering from diabetes must clearly limit and control their intake of sugar. One common approach is to develop a diet plan with, for example, meal recipes and snack limitations. These plans are often provided by nutritional therapists. However, a diet plans are difficult to maintain and are often too restrictive. It often means the food preparer must prepare separate meals for the patient than for the rest of the household. Diet plans are complicated enough that they are often abandoned after a short period of time, whereas the chronic disease continues for years. An option for the patients and the food preparer may be to try to simply increase the consumption of foods with disease-healthy ingredients and avoid or reduce the consumption of foods with disease-harmful ingredients. The ingredients in unprocessed or minimally processed foods are usually easily recognized, foods such as fruits, vegetables, meats, etc. However, the ingredients in processed food are not that apparent, foods such as snacks, take-out food from a restaurant, packaged frozen foods, and canned goods. One can look at food labels, but they only contain some information about a limited set of ingredients such as carbohydrates, fat, protein, sugar, and sodium. However, the disease-harmful ingredients often will not be listed. For example, a processed food might contain phosphorus in a quantity that would be inadvisable for consumption by someone with chronic kidney disease, but the term "phosphorus" will not be listed on the food label. A new approach to medical nutritional therapy is needed which is easy to maintain, an approach that increases the food products in a household with are disease-healthy ingredients and reduces or eliminates food products with disease-harmful ingredients. An approach that provides satisfying ingredients to all members of the household while providing effective nutritional therapy for the patient.

SUMMARY

In accordance with some implementations, a system comprises: at least one compute node configured to create a patient profile, select at least one nutritional prescription template based on the patient profile, calculate a patient-specific nutritional prescription based on the patient profile and the selected nutritional prescription template, and calculate recommendations for food products based on the patient-specific nutritional prescription.

In accordance with some implementations, a method comprises: creating a patient profile; selecting at least one nutritional prescription template based on the patient profile; calculating a patient-specific nutritional prescription based on the patient profile and the selected nutritional prescription template; and calculating recommendations for food products based on the patient-specific nutritional prescription.

In accordance with some implementations, a non-transitory computer-readable storage medium stores instructions that when executed by at least one compute node causing the compute node to perform a method for calculating recommendations for food products, the method comprising: creating a patient profile; selecting at least one nutritional prescription template based on the patient profile; calculating a patient-specific nutritional prescription based on the patient profile and the selected nutritional prescription template; and calculating recommendations for available food products based on the patient-specific nutritional prescription.

This summary is not intended to limit the scope of the claims or the disclosure. Other aspects, features, and implementations will become apparent in view of the detailed description and figures, and all the examples, aspects, implementations, and features can be combined in any technically possible way.

DETAILED DESCRIPTION

Some aspects, features, and implementations described herein may include machines such as computers, electronic components, optical components, and processes such as computer-implemented procedures and steps. It will be apparent to those of ordinary skill in the art that the computer-implemented procedures and steps may be stored as computer-executable instructions on a non-transitory computer-readable medium. Furthermore, it will be understood by those of ordinary skill in the art that the computer-executable instructions may be executed on a variety of tangible processor devices, i.e., physical hardware. For practical reasons, not every step, device, and component that may be part of a computer or data storage system is described herein. Those of ordinary skill in the art will recognize such steps, devices, and components in view of the teachings of the present disclosure and the knowledge generally available to those of ordinary skill in the art. The corresponding machines and processes are therefore enabled and within the scope of the disclosure.

Figure 1:
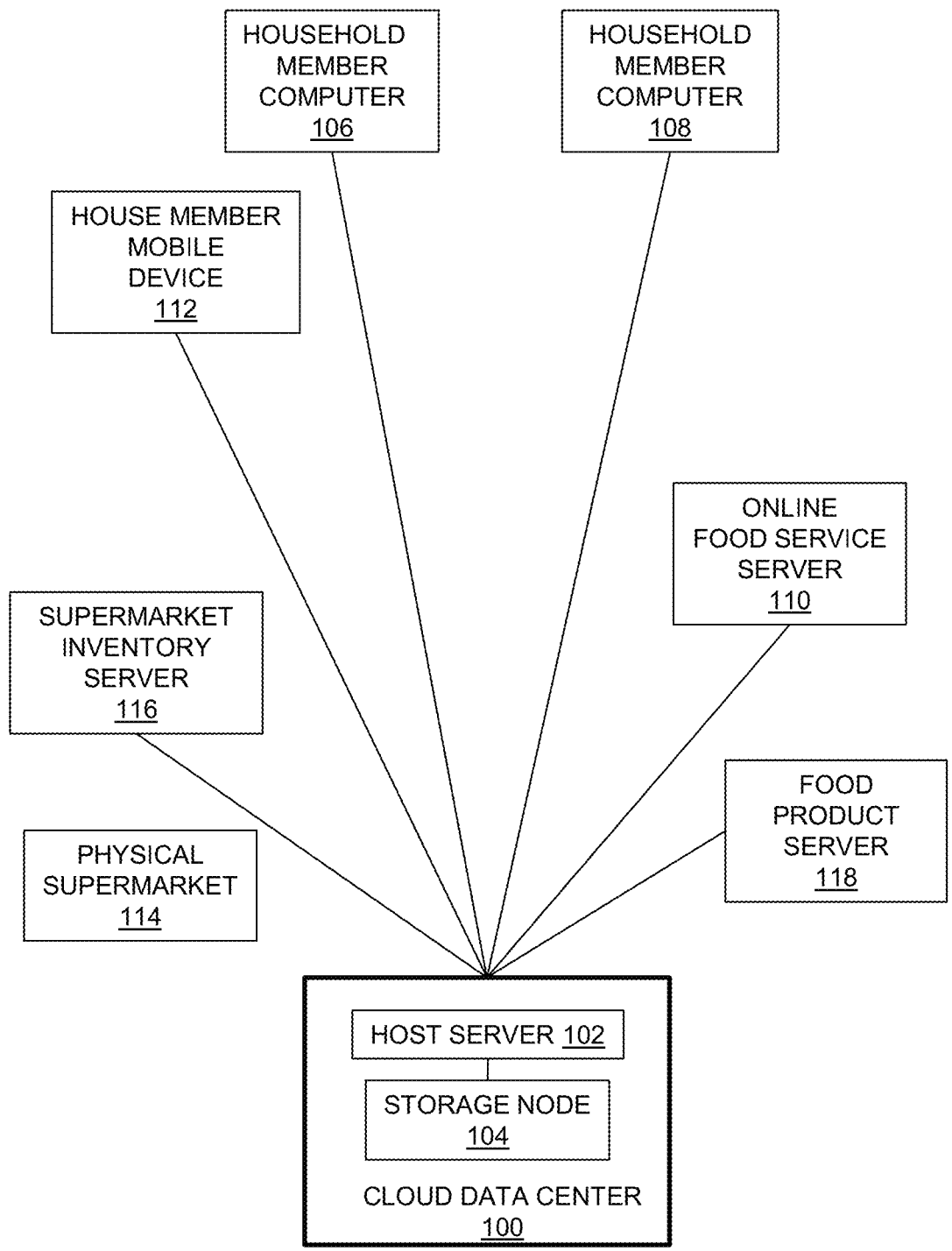
FIG. 1 illustrates physical infrastructure for providing medical nutritional therapy as a service.

FIG. 1 illustrates physical infrastructure for providing medical nutritional therapy as a service. A cloud-based data service 100 for providing services to multiple households includes a cloud-based host server 102 and a storage node 104. The storage node may include direct-attached storage (DAS), network-attached storage (NAS), or any of a variety of storage architectures that enable data to be maintained on arrays of non-volatile drives and accessed by the host server. The host server may be a member of a server cluster. Each server in the cluster includes microprocessors, computer-readable memory, and hypervisors or containers for supporting virtual machines or guest operating systems for running instances of host applications for automating medical nutritional therapy services. The host application instances for providing medical nutritional therapy services will be referred to below as pantry application instances. The servers of the server cluster are configured to communicate with household computers 106, 108 such as PCs and tablets of the respective households of which treated patients are members. A household includes at least one patient undergoing nutritional therapy for a chronic disease and zero or more other participating members who live and eat together. The host server 102 and household computer 108 are configured to communicate with an online supermarket server 110 to manage and replenish a pantry inventory via online food shopping. A mobile device 112, such as a smartphone, is configured to communicate with the host server 102 to coordinate with pantry application when shopping at a physical supermarket 114.

Figure 2:
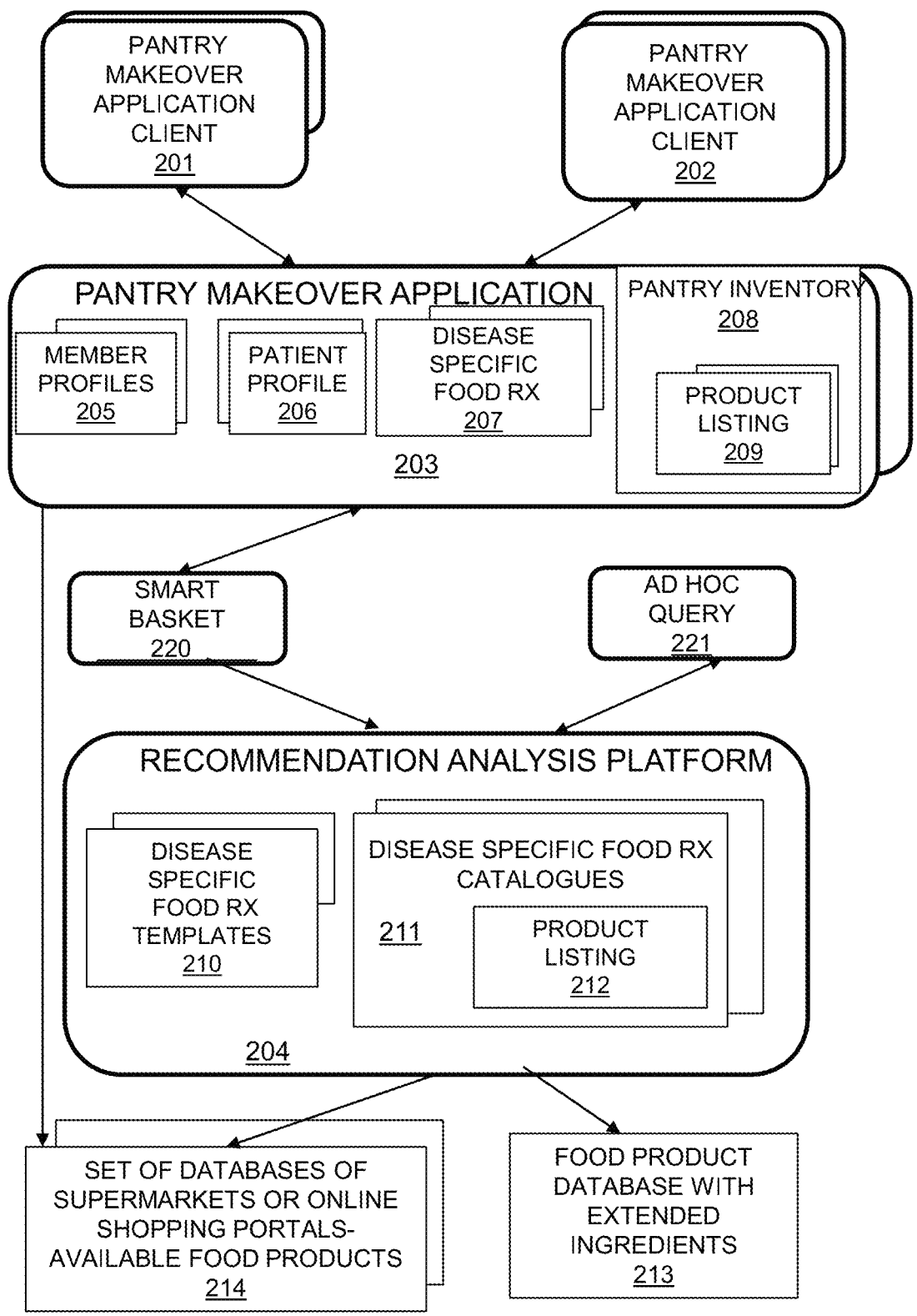
FIG. 2 illustrates software applications and data associated with the infrastructure of FIG. 1.

Referring to FIGS. 1 and 2, pantry application client instances 201, 202 run on a household computer 106 and interface to a pantry server application instance 203, which runs on the host server 102. There can be numerous pantry application instances serviced by many pantry application client instances. A smart basket application 220 runs on mobile computing device 112. The pantry makeover application 203 and the recommendation analysis platform 204 maintains various databases on the storage node 104. The pantry makeover application maintains the following datastores: member profiles 205, patient profiles 206, disease specific Rx's (i.e., nutritional prescriptions) 207, and the household pantry inventory 208, which includes a product listing of a set of food products 209. The recommendation analysis platform 204 maintains the following datastores: a library of disease specific Food Rx templates 210 and a set of disease specific catalogues 211 that have a structure of the categories, sub-categories and food-groups that are related to a specific disease and also maintain a product listing 212 that mirrors the food products stored in the product inventory 209. Each nutritional therapy prescription template 210 is uniquely associated with a particular chronic condition and includes records of disease-harmful food ingredients, disease-healthy food ingredients, acceptable or recommended amounts or quantities of those food ingredients, acceptable frequency of consumption, and logic or rules for calculating inclusion and exclusion of those food ingredients in the diet of a patient with a specific chronic condition. A nutritional therapy prescription template of a chronic disease combined with of the profile of a patient, i.e., a member of the household that is needing treatment for a chronic disease, enables the generation of a patient-specific nutritional therapy prescription 207. An analysis and combination of all patients and all participating member profiles and all generated patient-specific nutritional prescription enables the generation of a household nutritional prescription and a household profile. The household nutritional prescription and the household profile are used by the recommendation analysis platform in the processes that produce recommendations for a food product. The patient profiles 206 have information about patient including: the patient's chronic disease(s) that is be treated, other chronic disease and conditions, medications, the biometrics of the patient, a characterization of the emotional and motivational characteristics of the patient, a record of biomarkers associated with the chronic disease, and the symptom status and disease stage of the treated chronic disease. The profile includes food product preferences. Positive preferences represent foods that are liked by the patient, negative preferences are for foods that are disliked. Preferences can be for a category, a sub-category, a food-group, or a specific food product. The patient can include food products that must be excluded from his or her diet and food products that should never be excluded. There can be members in the household that want to support the nutritional therapy for patients but also wish that their physical condition and food preferences are considered. For these participating members, a member profile 205 is created. Member profiles have less information than a patient profile, but they include the members biometrics, physical conditions, emotional characterization, and food preferences. The extended foods labels that are contained in the nutritional prescription template and in the generated patient-specific nutritional prescriptions include detailed records of ingredients in a food product. They may also contain health-related facts for a food product, such as nutritional calculations and information that is usually not present on the printed labels on the food product. The extended food labels may also indicate a single serving amount and the number of servings in the food product. The extended food labels are obtained by the recommendation analysis platform from an external database 213. Recommendations may be partially based on nutritional calculations that are not represented on the printed labels on food product packaging. For example, starting with two similar products that each contain 10 grams of sugar, the amounts of sugar are normalized for comparison by calculating the amount of sugar in a single serving size of each food product. The recommendation analysis platform also considers the amounts of beneficial ingredients such as fiber that may, or may not, be on the printed packaging label. The normalized amounts are used to calculate a net-of-beneficial ingredient result. For example, if the first food product has 10 grams of sugar and 5 grams of fiber and the second food product has 8 grams of sugar and 2 grams of fiber for the newly normalized serving sizes, then the food product having the lowest sugars net of fiber would be recommended for a reduced sugar food Rx, in this case the first food product with 10−5=5 grams net is selected over the second food product which has 8−2=6 grams net.

Figure 3:
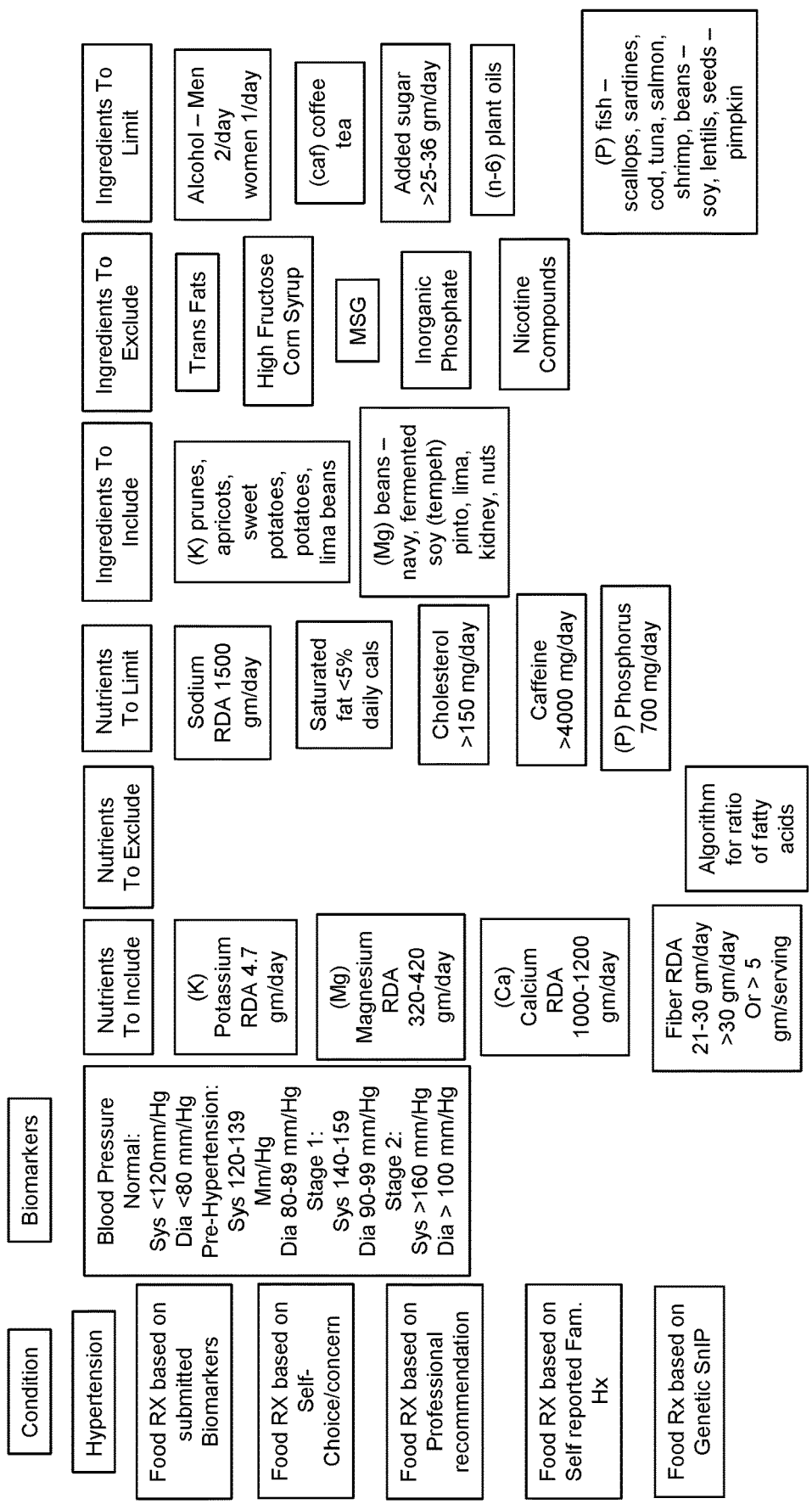
FIG. 3 illustrates a food Rx template.

FIG. 3 presents a diagrammatic example of a Food Rx template. The Food Rx templates are constructed from information provided by reliable medical resources. Column 1 identifies the chronic disease, in this case the Food Rx template for hypertension, along with some supporting material. Column 2 presents biomarkers for the disease so the status of the patient, in terms of the disease, can be ascertained. Column 5 presents the nutrients that should be included in a nutritional diet for hypertension, plus the recommended dietary allowance (RDA) amount for that nutrient. Column 6 presents food that should be excluded. In this case the exclusion is determined by an algorithm that computes the ratio of fatty acids. If the ratio is too high, that food should be excluded. Column 7 presents nutrients that should be limited along with a formula describing the limit. Columns 8, 9, and 10 represent a key value of the Food Rx template. The nutrient values are transformed into ingredients. Column 8 presents ingredients that should be included in the patient's diet. Column 9 presents ingredients that should be excluded. Column 10 presents ingredients whose daily intake should be limited.

Figure 4:
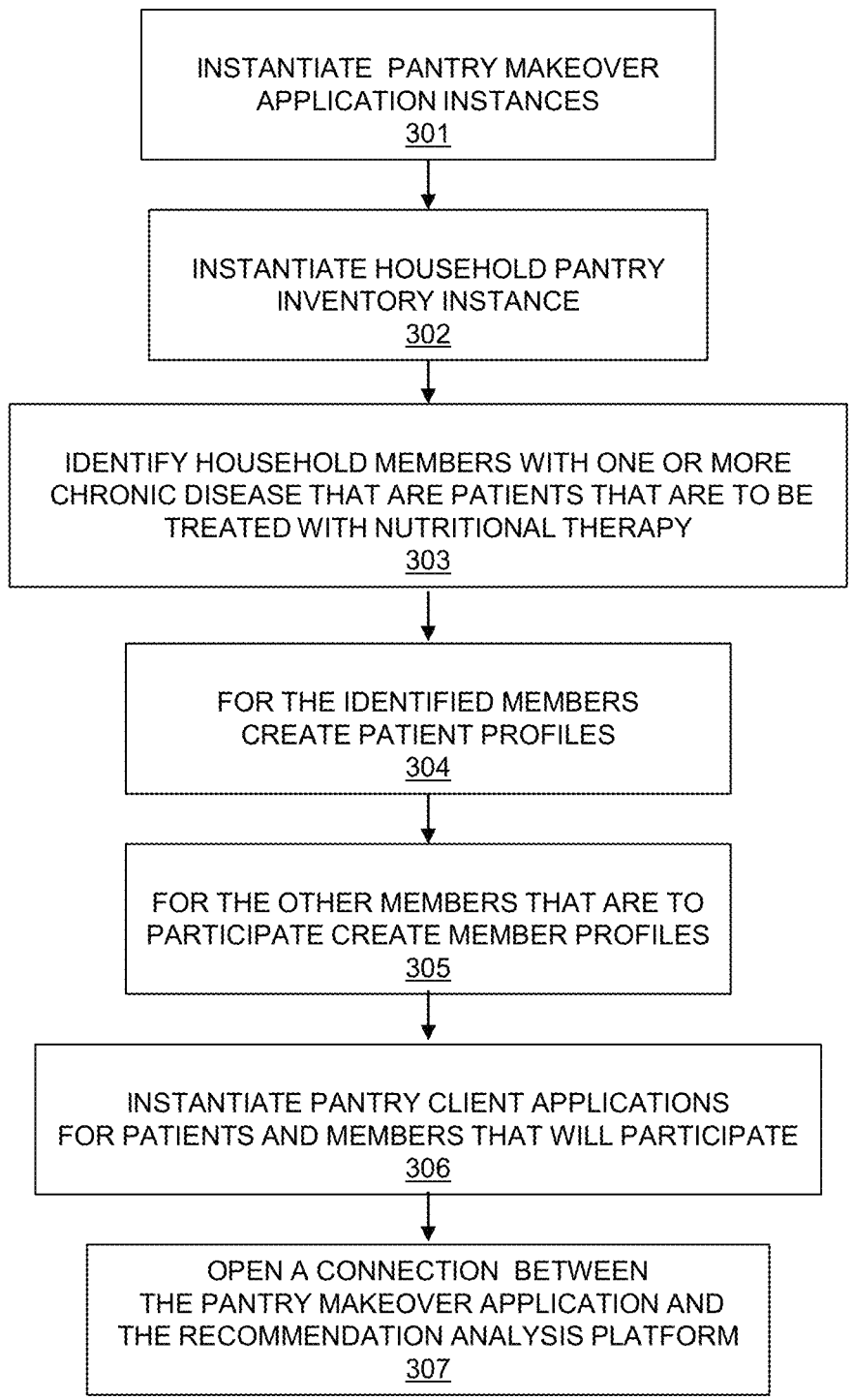
FIGS. 4 through 15 illustrate how the system functions.

FIG. 4 illustrates the steps taken to initializing the computer applications that will be used to provide nutritional therapy to patients in a household with chronic disease. Step 301 instantiates an instance of the pantry makeover application 203 that provides the basic services for providing nutritional therapy by improving the household food storage. Step 302 instantiates an instance of the Pantry Inventory 208. The Pantry Inventory keeps records of all foods processed including food processed from the household food storage and new food that are potentially going to be added to the Household food storage. These records include product recommendations and the follow-up action for those recommendations. Step 303 records the ID's and other identifies for members of the household that have one or more chronic diseases, who whose diet should improve as part of a program of nutritional therapy, who will participate as patients. Step 304 provides the interactive forms to create patient profiles 206 offered by the Pantry Makeover Application. The completed profiles are then stored in the Pantry Makeover Application's datastore. Patients may ask a medical professional to help with the forms or review their input. Step 305 provides the interactive forms for non-patient participating member profiles 205. Participating members can be involved in a number of different roles. The member profiles are specialized depending on the role of the participating member. There are participating members that perform needed functions for the nutritional therapy process, e.g., food preparer, shopper. There are participating members that are involved because they care about their own wellness. In fact, there are scenarios were there are no patients, just a set of household members interested in improving their wellness. The Pantry Makeover Applications takes their wellness aspirations into account when making food product choices. And there are participating members that just want to be involved and want to be helpful. Step 306 installs and instantiates a pantry client application on the devices of choice, such as PCs, tablets, smartphones, used by each of the participating member and patients. The pantry client applications are thin applications that provide a well-designed user interface in front of the cloud-based pantry makeover application. A web interface is also provided so access can be available wherever an internet connection can be made. Step 307 establishes a connection with the Recommendation Analysis Platform so that recommendations can be requested by the Pantry Makeover application and returned.

Figure 5:
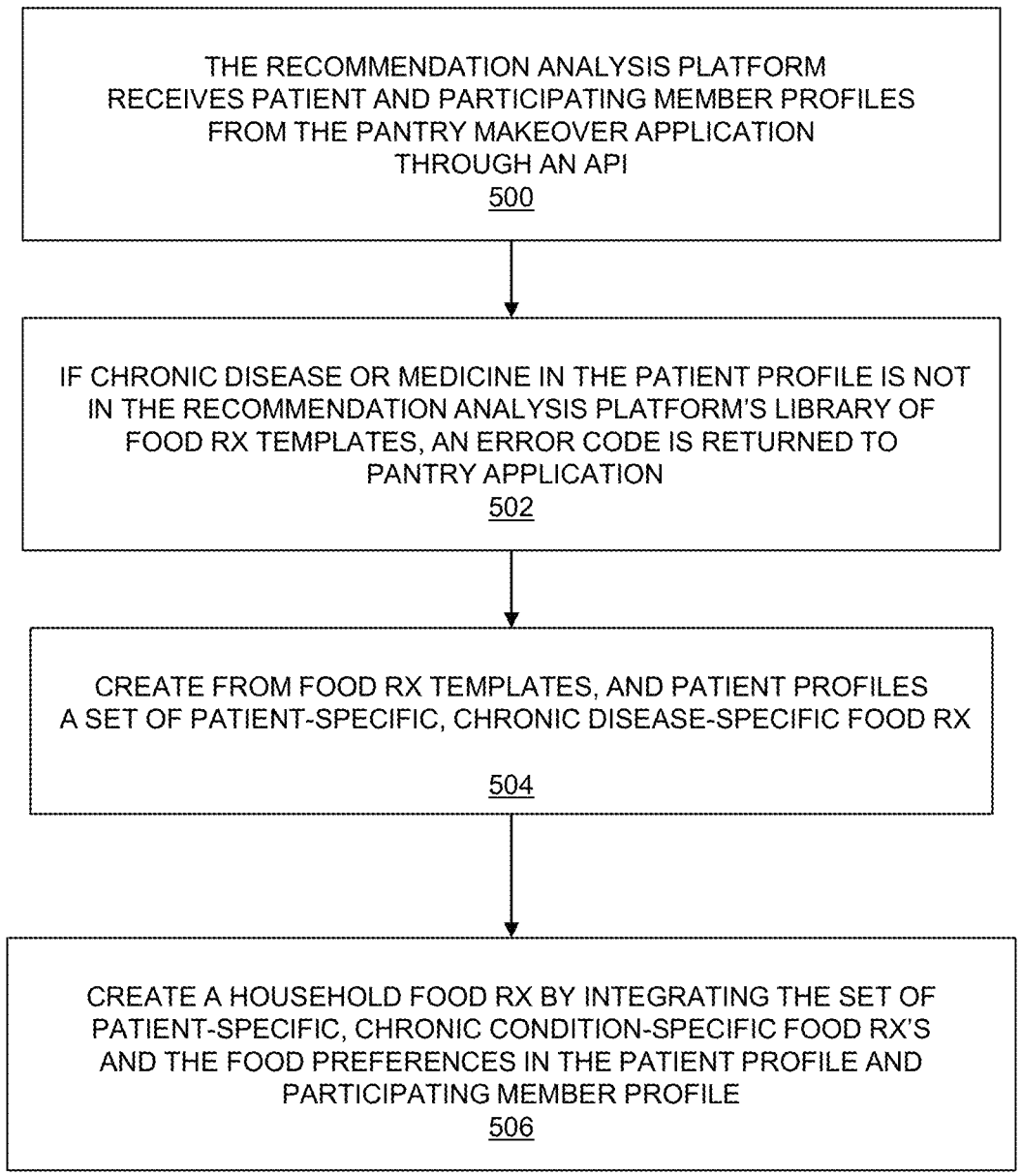

Referring to FIG. 5, step 500 is the recommendation analysis platform receiving patient and participating member profiles from the pantry makeover application through an API. Step 502 is returning an error code to the pantry application if the chronic disease or medicine in the patient profile is not in the recommendation analysis platform library of food Rx templates. Step 504 creating a set of patient-specific, chronic disease-specific, food Rxs from the food Rx templates and patient profiles. Step 506 is creating a household food Rx by integrating the set of patient-specific, chronic condition-specific food Rxs and the food preferences in the patient profile and participating member profile.

Figure 6:
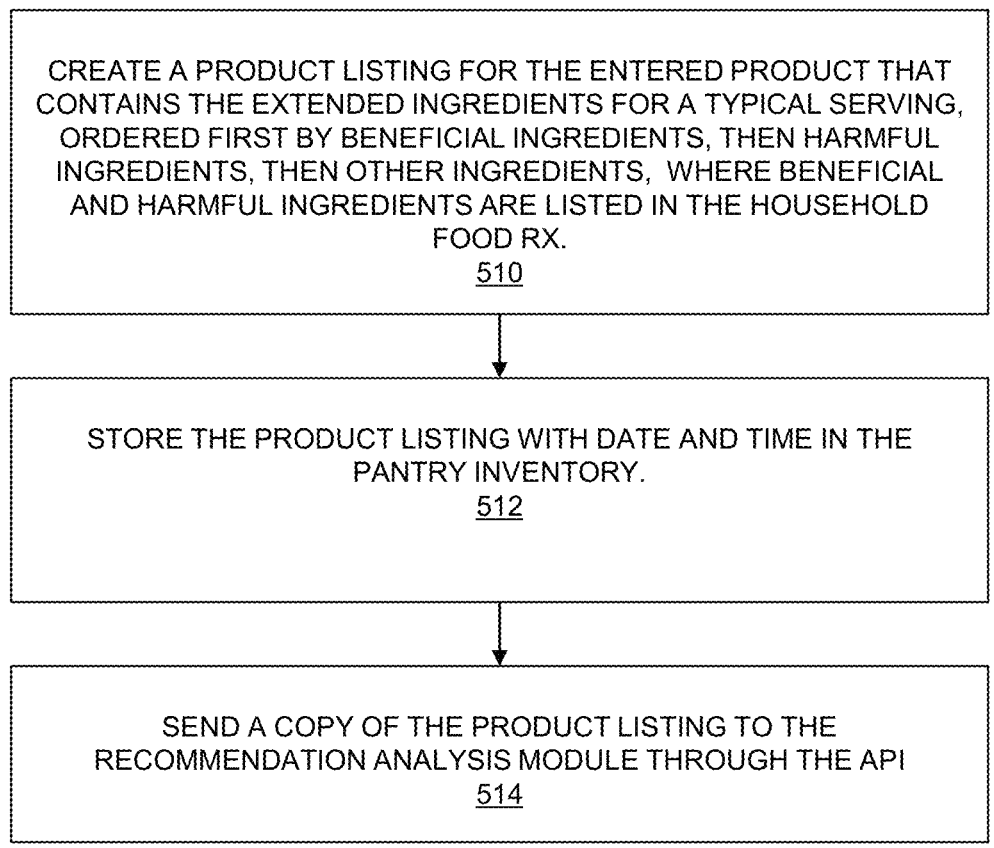

Referring to FIG. 6, step 510 is creating a product listing for the entered product that contains the extended ingredients for a typical serving, ordered first by beneficial ingredients, then harmful ingredients, then other ingredients, where beneficial and harmful ingredients are listed in the household food Rx. Step 512 is storing the product listing with date and time in the pantry inventory. Comparable listings may exist, creating a history of the entered product. Step 514 is sending a copy of the product listing to the recommendation analysis module through the API.

Figure 7:
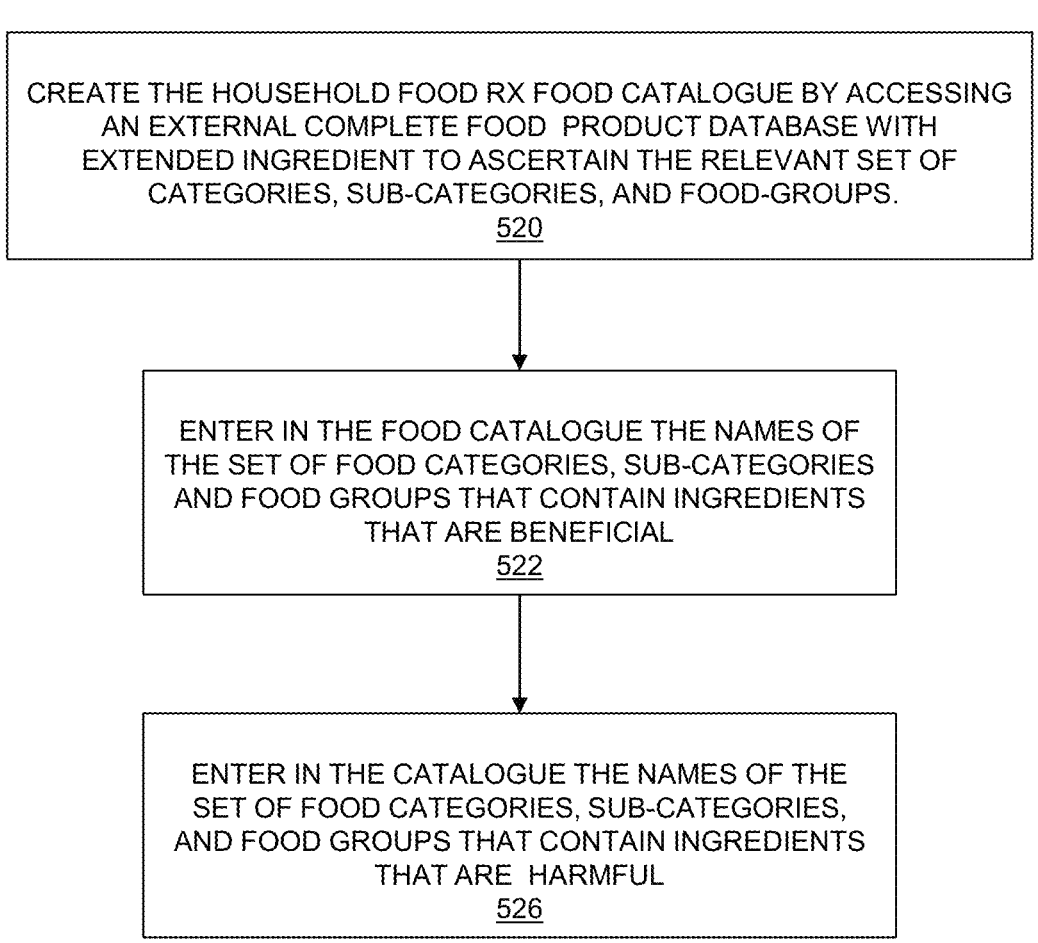

Referring to FIG. 7, step 520 is creating the household food Rx food catalogue by accessing an external complete food product database with extended ingredient to ascertain the relevant set of categories, sub-categories, and food-groups. Step 522 is entering the names of the set of food categories, sub-categories and food groups that contain ingredients that are beneficial in the food catalogue. Step 526 is entering the names of the set of food categories, sub-categories, and food groups that contain ingredients that are harmful in the catalogue.

Figure 8:
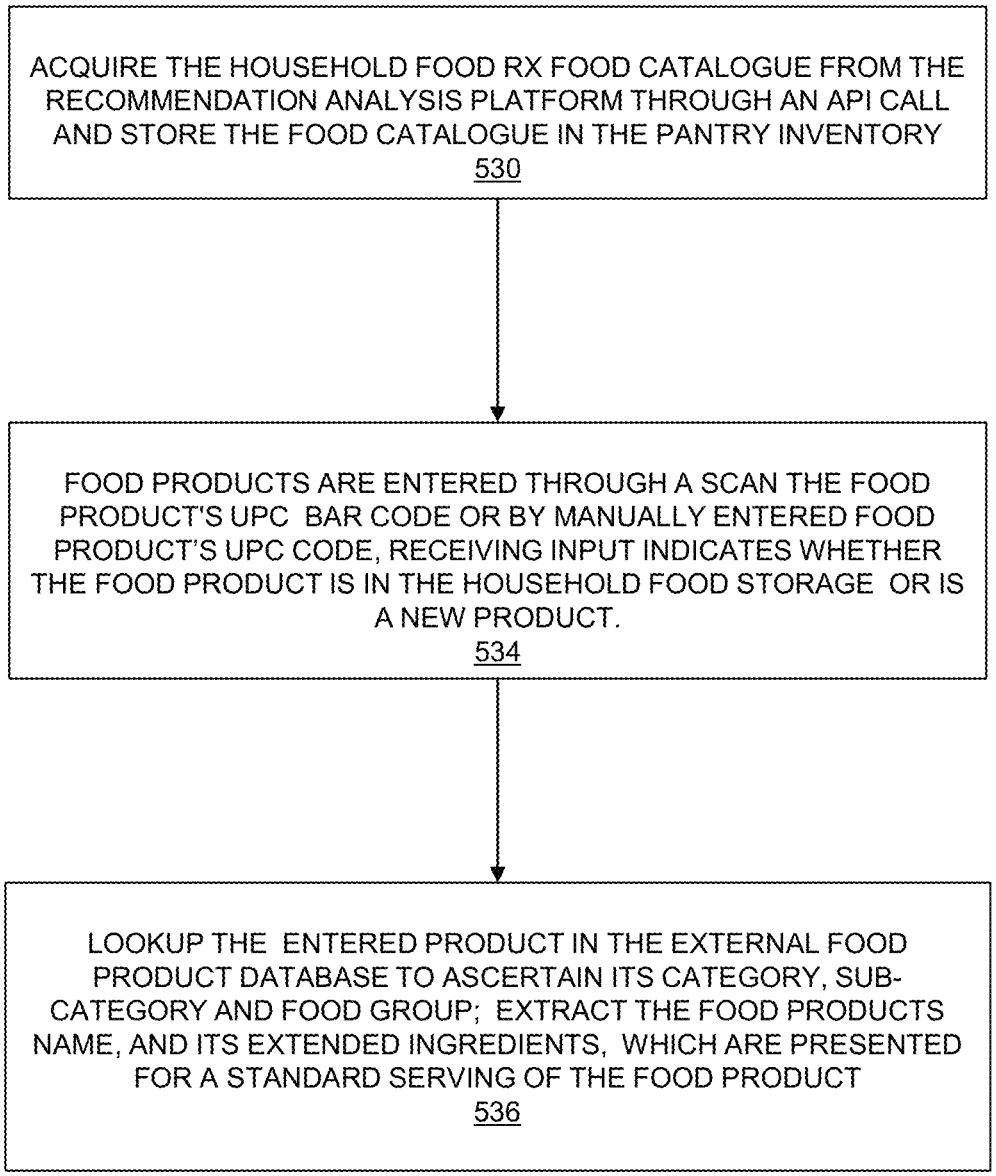

Referring to FIG. 8, step 530 is acquiring the household food Rx food catalogue from the recommendation analysis platform through an API call and storing the food catalogue in the pantry inventory. Step 534 is identifying food products by scanning or manually entering the UPC bar code on the food product packaging. The user indicates whether the food product is in the household food storage or is a new product. Step 536 is performing a lookup of the entered food product in the external food product database to ascertain its category, sub-category, and food group. The Food product name, extended ingredients, and standard serving are obtained.

Figure 9:
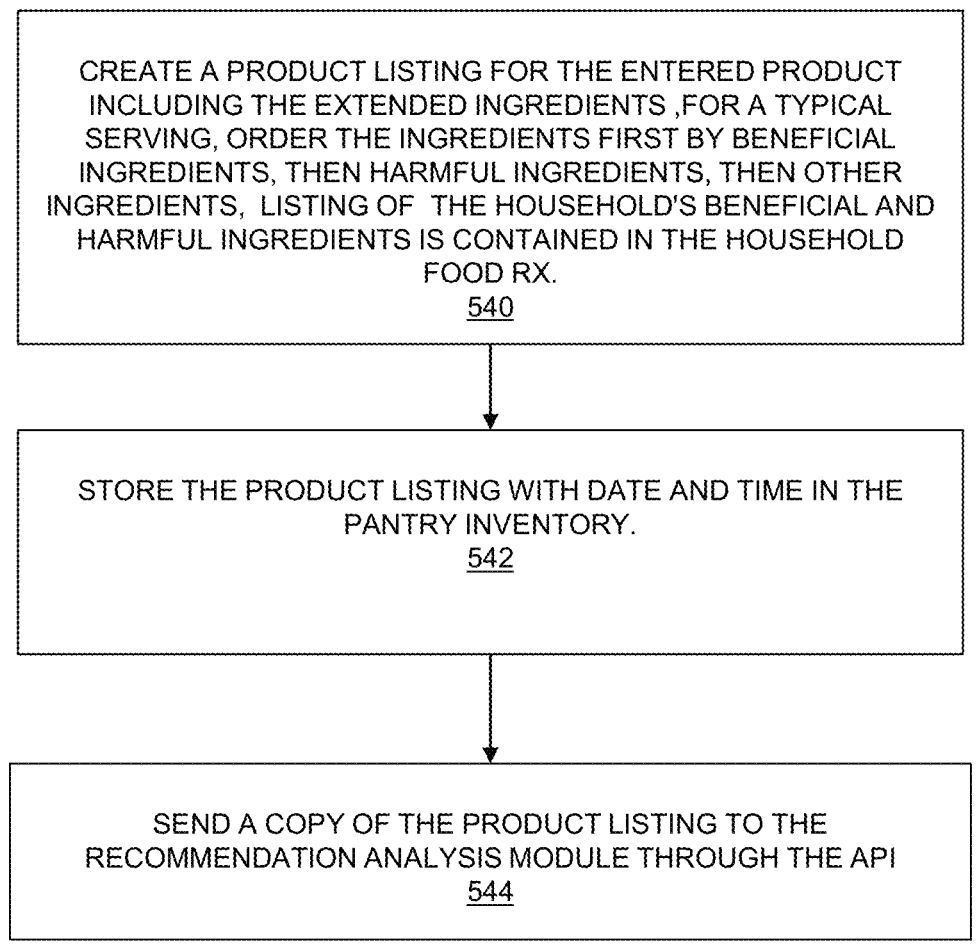

Referring to FIG. 9, step 540 is creating a food product listing for the entered food product, including a representation of the extended ingredients ordered first by beneficial ingredients, then harmful ingredients, then other ingredients. The listing of the household's beneficial and harmful ingredients is contained in the household food Rx. Step 542 is storing the food product listing with date and time in the pantry inventory. Step 544 is sending a copy of the food product listing to the recommendation analysis module through the API.

Figure 10:
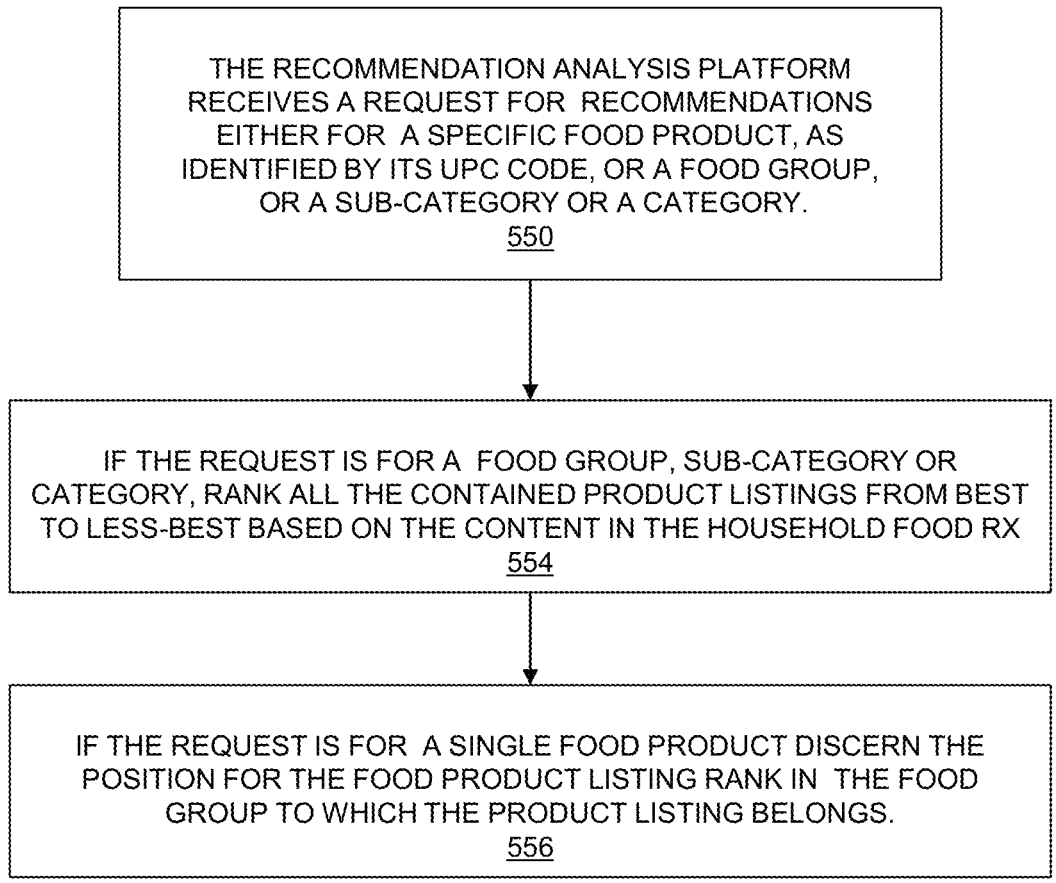

Referring to FIG. 10, in step 550 the recommendation analysis platform receives a request for recommendations, either for a specific food product as identified by its UPC code for a food group, or a sub-category, or a category. In step 554, if the request is for a food group, sub-category, or category, the contained food product listings are ranked from best to less-best based on the content in the household food Rx. In step 556 if the request is for a single food product, then the position for the food product listing rank in the food group to which the food product listing belongs is determined.

Figure 11:
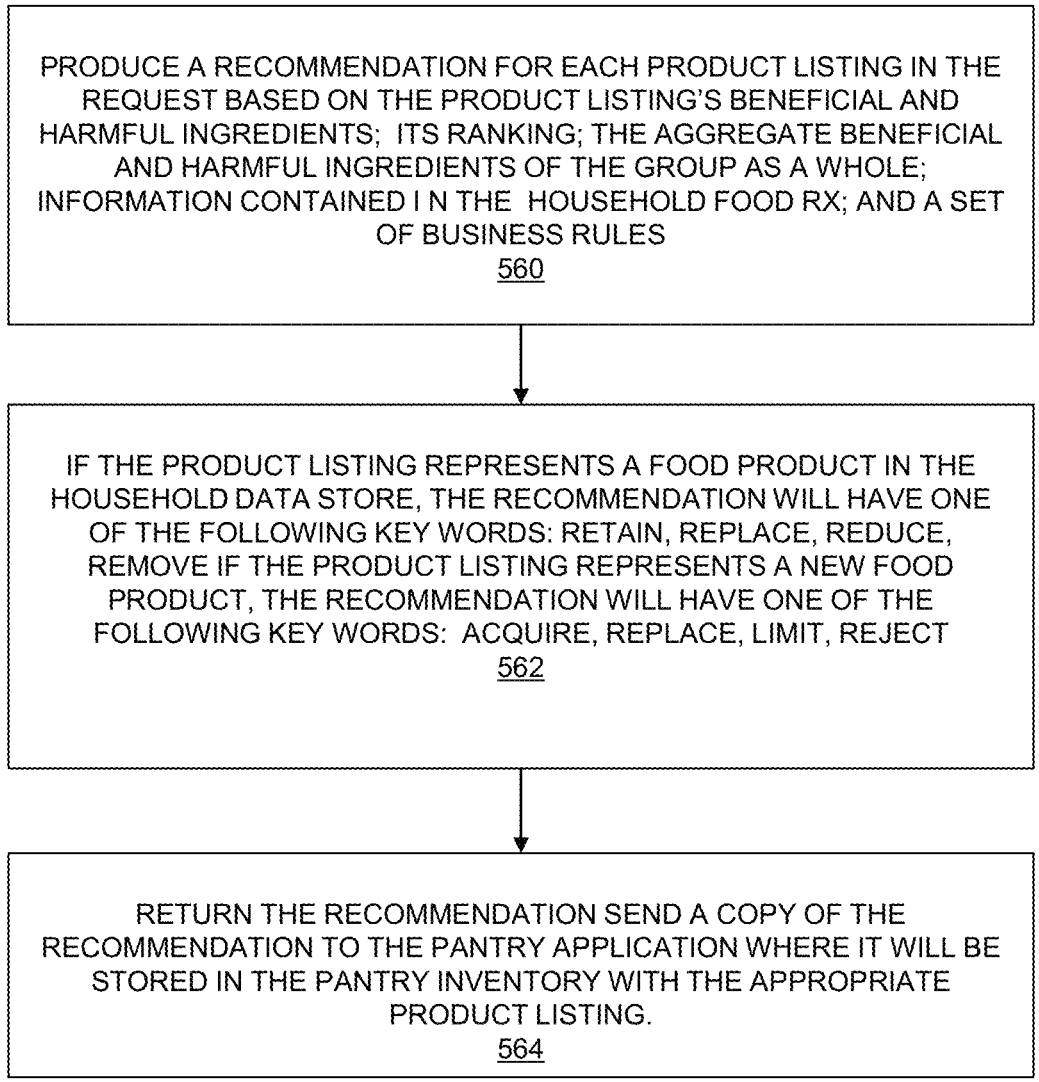

Referring to FIG. 11, step 560 is calculating a recommendation for each food product listing in the request based on the food product listing beneficial and harmful ingredients, rank, aggregate beneficial and harmful ingredients of the group as a whole; information contained in the household food Rx, and a set of business rules. As indicated in step 562, if the food product listing represents a food product in the household data store, the recommendation may have one of the following key words: Retain, Replace, Reduce, Remove. If the product listing represents a new food product, the recommendation may have one of the following key words: Acquire, Replace, Limit, Reject. Step 564 is sending a copy of the recommendation to the pantry application where it is stored in the pantry inventory with the appropriate food product listing.

Figure 12:
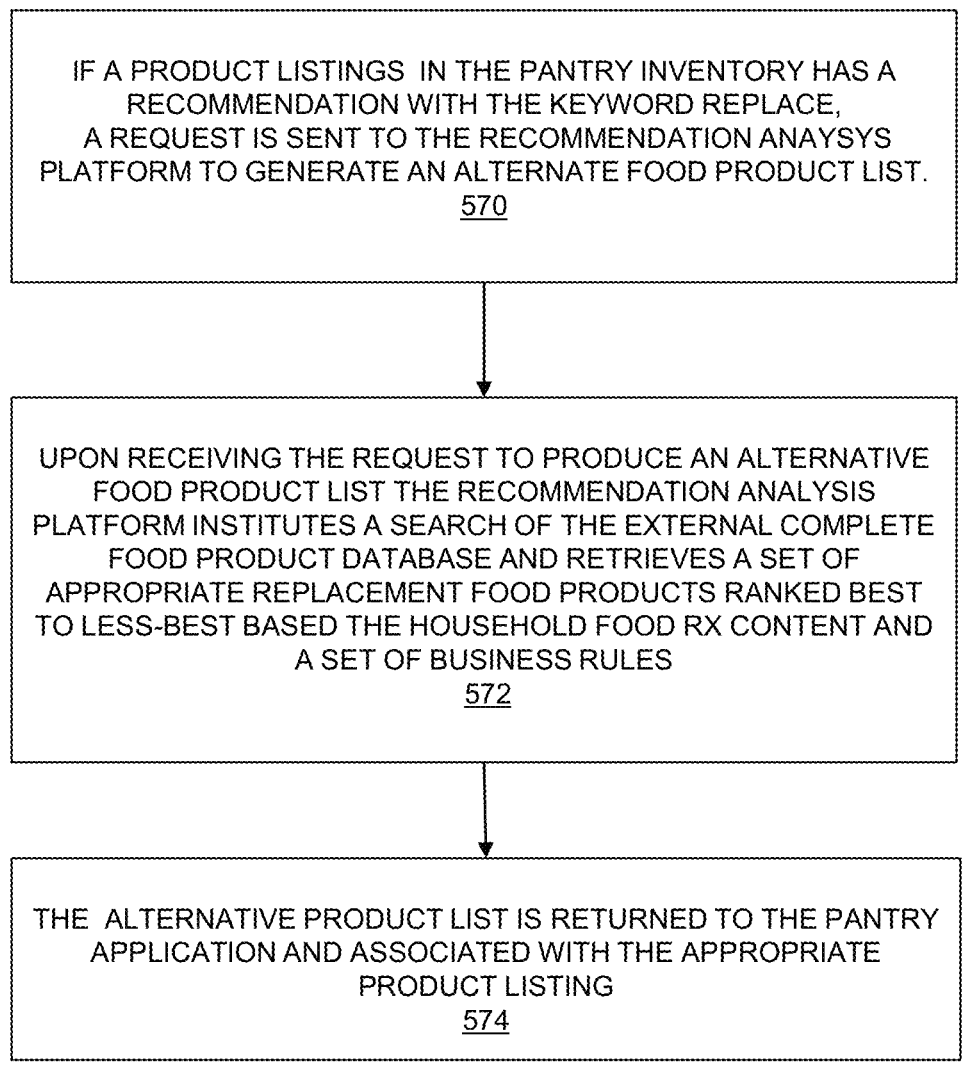

Referring to FIG. 12, if a food product listing in the pantry inventory has a recommendation with the keyword Replace, a request is sent to the recommendation analysis platform to generate an alternate food product list as indicated in step 570. Upon receiving the request to produce an alternative food product list, the recommendation analysis platform institutes a search of the external complete food product database and retrieves a set of appropriate replacement food products ranked best to less-best based the household food Rx content and a set of business rules as indicated in step 572. The alternative product list is returned to the pantry application and associated with the appropriate product listing as indicated in step 574. The recommendations returned are associated with the specific store being shopped for alternatives.

Figure 13:
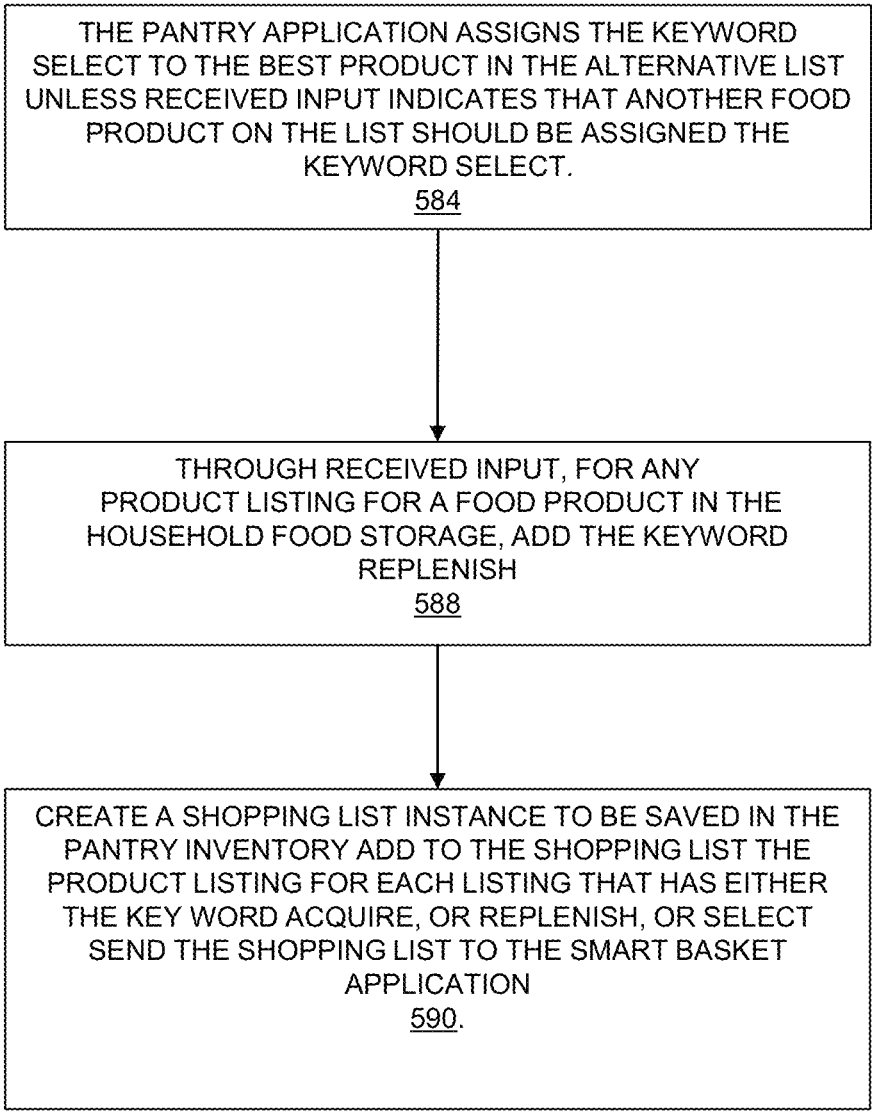
Figure 14:
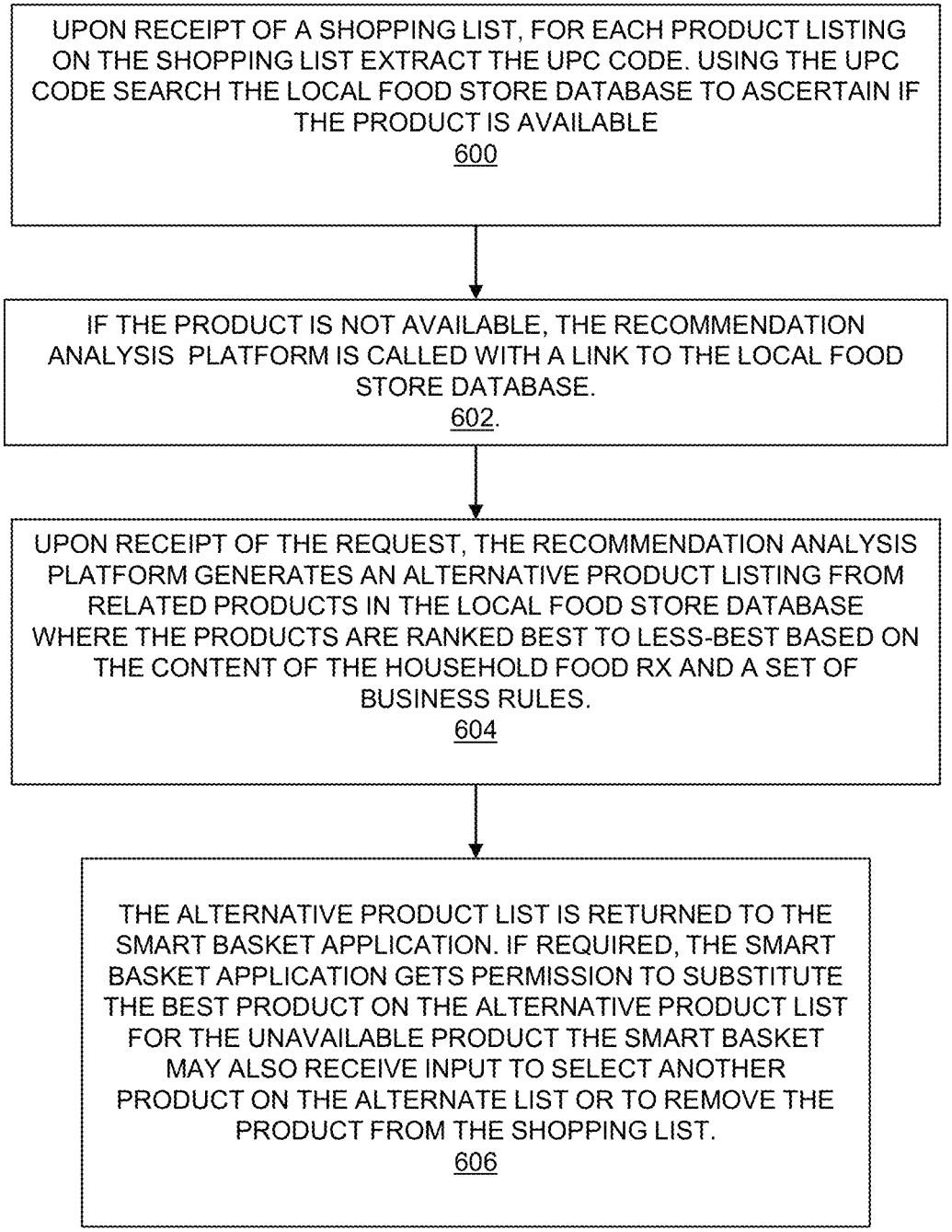

Referring to FIG. 13, in step 584 the pantry application assigns the keyword Select to the best product in the alternative list unless received input indicates that another food product on the list should be assigned the keyword Select. In step 588, through received input, for any product listing for a food product in the household food storage, the keyword Replenish is added. Step 590 is creating a shopping list instance to be saved in the pantry inventory. The product listing for each listing that has either the key word Acquire, or Replenish, or Select is added to the shopping list. The shopping list is sent to the smart basket application Referring to FIG. 14, step 600 extracting the UPC code for each product listing on the shopping list. The UPC codes are used to search the local food store database to ascertain if the product is available. As indicted in step 602, if the product is not available then the recommendation analysis platform is called with a link to the local food store database. In step 604 the recommendation analysis platform generates an alternative product listing from related products in the local food store database. The products are ranked best to less-best based on the content of the household food Rx and a set of business rules. The alternative product list is returned to the smart basket application in step 606. If required, the smart basket application obtains permission to substitute the best product on the alternative product list for the unavailable product. The smart basket may also receive input to select another product on the alternate list or to remove the product from the shopping list.

Figure 15:
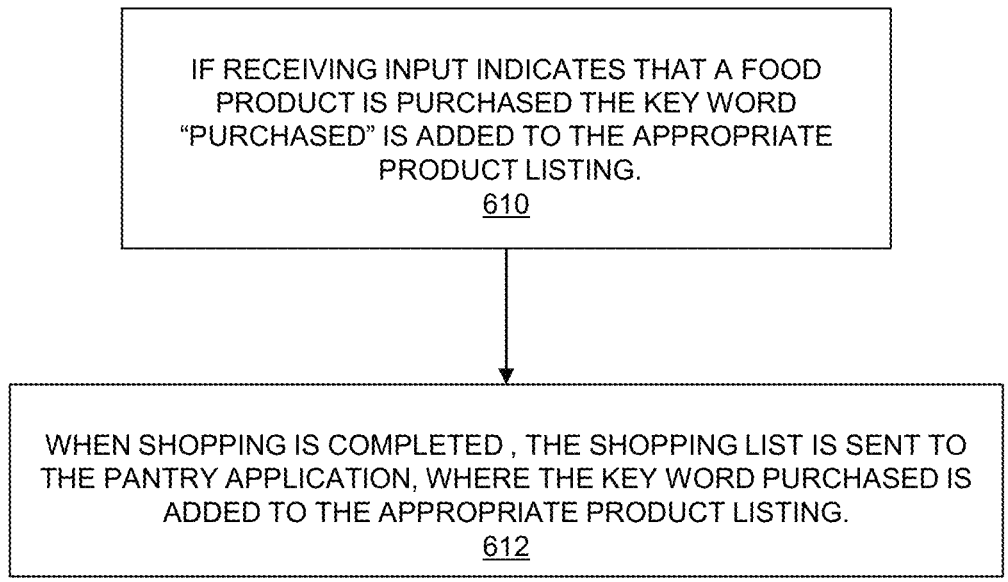

Referring to FIG. 15, the key word "Purchased" is added to the appropriate product listing for each food product that is purchased as indicated in step 610. When shopping is completed, the shopping list is sent to the pantry application, where the key word Purchased is added to the appropriate product listing as indicated in step 612. When shopping is completed, the shopping list is sent to the pantry application, where the key word Purchased is added to the appropriate product listing.

In view of the description above it will be apparent that some aspects of the invention advantageously support nutritional therapy by supporting pantry makeovers and food shopping. Food products that, unbeknownst to members of a household, contain harmful ingredients are identified and removed from household food storage. Food products that contain beneficial ingredients are recommended. Less harmful, more beneficial alternative food products are identified and suggested. Patients who are unable or unwilling to switch to a set meal plan that requires preparation of specific raw and minimally processed foods are guided to choosing more healthy food products based on their own preferences. For example, patients are guided away from consumption of food products that the patient might otherwise not realize are specifically unhealthy in view of their chronic condition. Further, patients are guided toward consumption of food products that the patient might otherwise not realize are specifically healthy in view of their chronic condition. By recommending more healthy alternative food products and recommending pantry inventory updates in response to updated, new, and discontinued food products, aspects of the invention help to generate and maintain nutritional prescriptions that are easier for patients to implement and maintain over longer periods of time. Further, the nutritional prescriptions are more easily developed and maintained for patients who have multiple chronic conditions and households in which multiple members have chronic conditions.

Specific examples have been presented to provide context and convey inventive concepts. The specific examples are not to be considered as limiting. A wide variety of modifications may be made without departing from the scope of the inventive concepts described herein. Moreover, the features, aspects, and implementations described herein may be combined in any technically possible way. Accordingly, modifications and combinations are within the scope of the following claims.

What is claimed is:

1. A method for controlling procurement of food products, comprising:
   a remote computer system prompting provision of information about a patient, including at least one chronic condition and food product preferences of the patient; and
   responsive to receipt of the information:
      creating an electronic patient profile from the information;
      selecting and loading at least one electronic nutritional prescription template from electronic data storage based on the chronic condition in the patient profile, the nutritional prescription template including a record of harmful ingredients and beneficial ingredients relative to the chronic condition; and
      calculating a patient-specific nutritional prescription based on the patient profile and the selected nutritional prescription template;
   scanning bar codes on food products in household food storage with a mobile device;
   querying a database of extended food labels based on the scanned bar codes with the remote computer system, the extended food labels comprising a record of all ingredients of individual food products, including the beneficial ingredients that are not listed on the food products and the harmful ingredients that are not listed on the food products;
   identifying and physically removing from household food storage at least one of the food products in household food storage that contains an unlisted harmful ingredient identified in the database of extended food labels and the patient-specific nutritional prescription; and
   physically adding to household food storage at least one food product determined to be a beneficial food product based on the patient-specific nutritional prescription and the database of extended food labels;
   with the mobile device:
   causing the remote computer system to identify potential replacement food products for a first food product by wirelessly transmitting, to the remote computer system, a command including information that identifies an individual food store from which food products are procured and a code that represents the first food product;
   with the remote computer system in response to receipt of the command:
   querying the database of extended food labels based on the code that represents the first food product and the food product preferences to identify the potential replacement food products;
   querying a food store inventory database of the food store and filtering the identified potential replacement food products by determining which of the potential replacement food products are available in inventory of the food store;
   calculating a ranked list of recommendations of the potential replacement food products that are available at the food store based on the patient-specific nutritional prescription and the extended food labels by normalizing amounts of the harmful ingredients and the beneficial ingredients in the potential replacement food products that are available at the food store and comparing the normalized amounts;

identifying a best-ranked food product of the ranked list of recommendations of the potential replacement food products that are available at the food store; and transmitting a shopping list update to the mobile device to prompt substitution of the best-ranked food product for the first food product; and with the mobile device responsive to the shopping list update:

updating a shopping list by adding the best-ranked food product and removing the first food product; and displaying the updated shopping list and procure the best-ranked food product.

2. The method of claim 1 further comprising calculating a household food prescription by integrating a plurality of patient-specific nutritional prescriptions.

3. The method of claim 1 further comprising scanning a bar code on packaging of the first food product to identify the first food product, and calculating and displaying a recommendation that the first food product is harmful to the patient and should not be consumed by the patient based on the first food product containing one of the harmful ingredients according to the database of extended food labels.

4. The method of claim 1 further comprising creating a pantry inventory with a listing of beneficial to the patient food products associated with the patient-specific nutritional prescription.

5. The method of claim 4 further comprising adding to the pantry inventory at least one limited consumption food product that can be consumed in limited amounts based on the patient-specific nutritional prescription and extended ingredients of that limited consumption food product.

6. A non-transitory computer-readable storage medium storing instructions that when executed by a computer cause the computer to perform steps of a method with a remote computer system and a mobile device for controlling food product procurement for providing medical nutritional therapy to at least one household member who is a patient, the method comprising:

with the remote computer system:

prompting provision of information about the patient, including at least one chronic condition and food product preferences of the patient; and responsive to receipt of the information:

creating an electronic patient profile from the information;

selecting and loading at least one electronic nutritional prescription template from electronic data storage based on the chronic condition in the patient profile, the nutritional prescription template including a record of harmful ingredients and beneficial ingredients relative to the chronic condition; and calculating a patient-specific nutritional prescription based on the patient profile and the selected nutritional prescription template;

scanning bar codes on food products in household food storage with the mobile device;

querying a database of extended food labels based on the scanned bar codes with the remote computer system, the extended food labels comprising a record of all ingredients of individual food products, including the beneficial ingredients that are not listed on the food products and the harmful ingredients that are not listed on the food products;

identifying and physically removing from household food storage at least one of the food products in household food storage that contains an unlisted harmful ingredient identified in the database of extended food labels and the patient-specific nutritional prescription; and physically adding to household food storage at least one food product determined to be a beneficial food product based on the patient-specific nutritional prescription and the database of extended food labels;

with the mobile device:

causing the remote computer system to identify potential replacement food products for a first food product by wirelessly transmitting, to the remote computer system, a command including information that identifies an individual food store from which food products are procured and a code that represents the first food product;

with the remote computer system in response to receipt of the command:

querying the database of extended food labels based on the code that represents the first food product and the food product preferences to identify the potential replacement food products;

querying a food store inventory database of the food store and filtering the identified potential replacement food products by determining which of the potential replacement food products are available at the food store;

calculating a ranked list of recommendations of the potential replacement food products that are available at the food store based on the patient-specific nutritional prescription and the extended food labels by normalizing amounts of the harmful ingredients and the beneficial ingredients in the potential replacement food products that are available at the food store and comparing the normalized amounts;

identifying a best-ranked food product of the ranked list of recommendations of the potential replacement food products that are available at the food store;

transmitting a shopping list update to the mobile device to prompt substitution of the best-ranked food product for the first food product; and with the mobile device responsive to the shopping list update:

updating a shopping list by adding the best-ranked food product and removing the first food product; and displaying the updated shopping list of and procure the best-ranked food product.

7. The non-transitory computer-readable storage medium of claim 6 wherein the method further comprises calculating a household food prescription by integrating a plurality of patient-specific nutritional prescriptions.

8. The non-transitory computer-readable storage medium of claim 6 wherein the method further comprises scanning a bar code on packaging of the first food product to identify the first food product, and calculating and displaying a recommendation that the first food product should not be consumed by the patient based on the first food product containing one of the harmful ingredients according to the database of extended food labels.

9. The non-transitory computer-readable storage medium of claim 6 wherein the method further comprises creating a pantry inventory with a listing of beneficial to the patient food products associated with the patient-specific nutritional prescription.

10. The non-transitory computer-readable storage medium of claim 9 wherein the method further comprises adding to the pantry inventory at least one limited consumption food product that can be consumed in limited amounts based on the patient-specific nutritional prescription and extended ingredients of that limited consumption food product.

11. A system for controlling food product procurement, comprising:
   at least one remote computer configured to:
      prompt provision of information about a patient, including at least one chronic condition and food product preferences of the patient; and
      responsive to receipt of the information:
         create an electronic patient profile from the information;
         select and load at least one electronic nutritional prescription template from electronic data storage based on the chronic condition in the patient profile, the nutritional prescription template including a record of harmful ingredients and beneficial ingredients relative to the chronic condition; and
         calculate a patient-specific nutritional prescription based on the patient profile and the selected nutritional prescription template;
   a mobile device configured to:
      scan bar codes on food products in household food storage;
      cause the remote computer to query a database of extended food labels based on the scanned bar codes, the extended food labels comprising a record of all ingredients of individual food products, including the beneficial ingredients that are not listed on the food products and the harmful ingredients that are not listed on the food products;
   means for physically removing from household food storage at least one of the food products in household food storage that contains an unlisted harmful ingredient identified in the database of extended food labels and the patient-specific nutritional prescription; and
   means for physically adding to household food storage at least one food product determined to be a beneficial food product based on the patient-specific nutritional prescription and the database of extended food labels;
   the mobile device further configured to cause the remote computer system to identify potential replacement food products for a first food product by wirelessly transmitting, to the remote computer system, a command including information that identifies an individual food store from which food products are procured and a code that represents the first food product;
   the remote computer system configured to respond to receipt of the command to:
      query the database of extended food labels based on the code that represents the first food product and the food product preferences to identify potential replacement food products;
      query a food store inventory database of the food store and filter the identified potential replacement food products by determining which of the potential replacement food products are available at the food store;
      calculate a ranked list of recommendations of the potential replacement food products that are available at the food store based on the patient-specific nutritional prescription and the extended food labels by normalizing amounts of the harmful ingredients and the beneficial ingredients in the potential replacement food products that are available at the food store and comparing the normalized amounts;
      identify a best-ranked food product of the ranked list of recommendations of the potential replacement food products that are available at the food store, where the harmful not listed on;
      transmit a shopping list update to the mobile device to prompt substitution of the best-ranked food product for the first food product; and
   the mobile device configured to respond to the shopping list update to:
      update a shopping list by adding the best-ranked food product and removing the first food product; and
      display the updated shopping list and procure the best-ranked food product.

12. The system of claim 11 wherein the at least one remote computer is configured to calculate a household food prescription by integrating a plurality of patient-specific nutritional prescriptions.

13. The system of claim 11 wherein at least one computer is configured to scan a bar code on packaging of the first food product to identify the first food product, and calculate and display a recommendation that the first food product should not be consumed by the patient based on the first food product containing one of the harmful ingredients according to the database of extended food labels.

14. The system of claim 11 wherein at least one computer is configured to create a pantry inventory with a listing of beneficial food products associated with the patient-specific nutritional prescription.

\* \* \* \* \*